United States Patent
Bloomquist et al.

(10) Patent No.: US 6,410,686 B1
(45) Date of Patent: *Jun. 25, 2002

(54) GALANIN RECEPTOR 2 PROTEIN

(75) Inventors: Brian T. Bloomquist, New Haven; Michael L. McCaleb, Madison; Linda J. Cornfield, Hamden; Heeja Yoo-Warren, Orange, all of CT (US)

(73) Assignee: Bayer Corporation, Pittsburgh, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/665,034

(22) Filed: Jun. 5, 1996

(51) Int. Cl.⁷ ......................... C07K 14/705; C12N 5/10; C12N 15/12; C12N 15/63

(52) U.S. Cl. ..................... 530/350; 435/69.1; 435/71.1; 435/71.2; 435/325; 435/252.3; 435/320.1; 435/471

(58) Field of Search .......................... 530/350; 435/69.1, 435/71.1, 71.2, 172.3, 325, 252.3, 320.1, 471

(56) References Cited

FOREIGN PATENT DOCUMENTS

| EP | 0711830 | 5/1996 |
| WO | 9522608 | 8/1995 |
| WO | 9726853 | 7/1997 |
| WO | 9803548 | 1/1998 |

OTHER PUBLICATIONS

Rieger et al. Glossary of Genetics and Cytogenetics, Fourth Edition, Springer–Verlag, pp. 16–19, 1976.*

Akabayashi, et al., "Galanin–containing neurons in the paraventricular nucleus: A neurochemical marker for fat ingestion and body weight gain", Proc. Natl. Acad. Sci. USA, 91: 10375–10379 (1994).

Bartfai, et al., "Galanin—A Neuroendocrine Peptide", Crit. Rev. Neurobiol., 7(3/4): 229–274 (1993).

Bockaert, J., "G Proteins and G–Protein–Coupled Receptors: Structure, Function and Interactions", Curr. Op. Neurobiol., 1: 32–42 (1991).

Burgevin, et al., "Cloning, Pharmacological Characterization, and Anatomical Distribution of a Rat cDNA Encoding for a Galanin Receptor", J. Mol. Neurosci., 6: 33–41 (1995).

Chen, et al., "Galanin receptor in plasma membrane of canine small intestinal circular muscle", Am. J. Physiol., 266: G113–117 (1994).

Crawley, Jacqueline N., "Biological Actions of Galanin, Regulatory Peptides", 59: 1–16 (1995).

Gillison, et al., "ADP Ribosylation by Cholera Toxin Indentifies Three G–Proteins that are Activated by the Galanin Receptor", Diabetes, 43: 24–32 (1994).

Habert–Ortoli, et al., "Molecular Cloning of a Functional Human Galanin Receptor", Proc. Natl. Acad. Sci. USA, 91: 9780–9783 (1994).

Merchenthaler, et al., "Anatomy and Physiology of Central Galanin–Containing Phatways", Prog. Neurobiol., 40: 711–769 (1993).

Skofitsch, et al., "Immunohistochemical Mapping of Galanin–Like Neurons in the Rat Central Nervous System", Peptides, 6: 509–546 (1985).

Wynick, et al., "Characterization of a high–affinity galanin receptor in the rat anterior pituitary: Absence of biological effect and reduced membrane binding of the antagonist M15 differentiate it from the brain/gut receptor", Proc. Natl. Acad. Sci. USA, 90: 4231–4235 (1993).

Zeng–Fa Gu, et al., "Interaction of Galanin Fragments with Galanin Receptors on Isolated Smooth Muscle Cells from Guinea Pig Stomach: Identification of a Novel Galanin Receptor Subtype", J. Pharmacol. Exp. Ther., 272: 371–378 (1995).

Habert–Ortoli, et al., Molecular Cloning of a Functional Human Galanin Receptor, Proc. Natl. Acad. Sci. USA, 91, 9780–9783 (1994).

Skofitsch, et al., Immunohistochemical Mapping of Galanin–Like Neurons in the Rat Central Nervous System, Peptides, 6, 509–546 (1985).

Merchenthaler, et al., Anatomy and Physiology of Central Galanin–Containing Phatways, Prog. Neurobiol., 40, 711–769 (1993).

Bartfai, et al., Galanin—A Neuroendocrine Peptide, Crit. Rev. Neurobiol., 7(3/4), 229–274 (1993).

Chen, et al., Galanin receptor in plasma membrane of canine small intestinal circular muscle, Am. J. Physiol., 266, G113–117 (1994).

Gillison, et al., ADP Ribosylation by Cholera Toxin Indentifies Three G–Proteins that are Activated by the Galanin Receptor, Diabetes, 43, 24–32 (1994).

Zeng–Fa Gu, et al., Interaction of Galanin Fragments with Galanin Receptors on Isolated Smooth Muscle Cells from Guinea Pig Stomach: Identification of a Novel Galanin Receptor Subtype, J. Pharmacol. Exp. Ther., 272, 371–378 (1995).

(List continued on next page.)

*Primary Examiner*—Prema Mertz (57) ABSTRACT

The present invention provides a novel galanin receptor protein, the GalR2 receptor. Also provided are the nucleic acid sequences encoding this novel receptor protein as well as methods for using this protein and its nucleic acid sequence, and methods useful for developing and identifying compounds for the treatment of diseases and disorders in which galanin is implicated. The importance of this discovery is manifested in the effects of galanin, which include antinociceptive activity, smooth muscle contraction, cardiovascular activity, pituitary hormone release, cognition, and increased food intake. Thus, this receptor protein is useful for screening for galanin agonist and antagonist activity for controlling these conditions.

2 Claims, 5 Drawing Sheets

OTHER PUBLICATIONS

Wynick, et al., Characterization of a high-affinity galanin receptor in the rat anterior pituitary: Absence of biological effect and reduced membrane binding of the antagonist M15 differentiate it from the brain/gut receptor, Proc. Natl. Acad. Sci. USA, 90, 4231–4235 (1993).

Akabayashi, et al., Galanin-containing neurons in the paraventricular nucleus: A neurochemical marker for fat ingestion and body weight gain, Proc. Natl. Acad. Sci. USA, 91, 10375–10379 (1994).

Jacqueline N. Crawley, Biological Actions of Galanin, Regulatory Peptides, 59, 1–16 (1995).

Burgevin, et al., Cloning, Pharmacological Characterization, and Anatomical Distribution of a Rat cDNA Encoding for a Galanin Receptor, J. Mol. Neurosci., 6, 33–41 (1995).

Joel Bockaert, G proteins and G-protein-coupled receptors: structure, function and interactions, Curr. Op. Neurobiol., 1, 32–42 (1991).

* cited by examiner

```
   1  TCGACCCACG CGTCCGCTCA AGTCTAAAGC AGAGCGAGTC CCAGGACTTG
  51  AGCGCGGGAA GCGAATGGAG TCAGGGTCAT TCGATTGCAC CTCTCTCGGC
 101  TGCGGGCCGG AGCGGGGTAC CATCCTACAC TCTGGGTGCT CCCTCCTCCT
 151  CCCGTCCCCC GCGCACCCCT GCCCTGGCTC CTGGAGCTCG GCAGTCTCGC
 201  TGGGGCGCTG CAGCGAGGGA GCAGCGTGCT CACCAAGACC CGGACAGCTG
 251  CGGGAGCGGC GTCCACTTTG GTGATACCAT GAATGGCTCC GGCAGCCAGG
 301  GCGCGGAGAA CACGAGCCAG GAAGGCGGTA GCGGCGGCTG GCAGCCTGAG
 351  GCGGTCCTTG TACCCCTATT TTTCGCGCTC ATCTTCCTCG TGGGCACCGT
 401  GGGCAACGCG CTGGTGCTGG CGGTGCTGCT GCGCGGCGGC CAGGCGGTCA
 451  GCACCACCAA CCTGTTCATC CTCAACCTGG GCGTGGCCGA CCTGTGTTTC
 501  ATCCTGTGCT GCGTGCCTTT CCAGGCCACC ATCTACACCC TGGACGACTG
 551  GGTGTTCGGC TCGCTGCTCT GCAAGGCTGT TCATTTCCTC ATCTTTCTCA
 601  CTATGCACGC CAGCAGCTTC ACGCTGGCCG CCGTCTCCCT GGACAGGTAT
 651  CTGGCCATCC GCTACCCGCT GCACTCCCGA GAGTTGCGCA CACCTCGAAA
 701  CGCGCTGGCC GCCATCGGGC TCATCTGGGG GCTAGCACTG CTCTTCTCCG
 751  GGCCCTACCT GAGCTACTAC CGTCAGTCGC AGCTGGCCAA CCTGACAGTA
 801  TGCCACCCAG CATGGAGCGC ACCTCGACGT CGAGCCATGG ACCTCTGCAC
 851  CTTCGTCTTT AGCTACCTGC TGCCAGTGCT AGTCCTCAGT CTGACCTATG
 901  CGCGTACCCT GCGCTACCTC TGGCGCACAG TCGACCCGGT GACTGCAGGC
 951  TCAGGTTCCC AGAGCGCCAA ACGCAAGGTG ACACGGATGA TCATCATCGT
1001  GGCGGTGCTT TTCTGCCTCT GTTGGATGCC CCACCACGCG CTTATCCTCT
1051  GCGTGTGGTT TGGTCGCTTC CCGCTCACGC GTGCCACTTA CGCGTTGCGC
1101  ATCCTTTCAC ACCTAGTTTC CTATGCCAAC TCCTGTGTCA ACCCCATCGT
1151  TTACGCTCTG GTCTCCAAGC ATTTCCGTAA AGGTTTCCGC AAAATCTGCG
1201  CGGGCCTGCT GCGCCCTGCC CCGAGGCGAG CTTCGGGCCG AGTGAGCATC
1251  CTGGCGCCTG GAACCATAG TGGCAGCATG CTGGAACAGG AATCCACAGA
1301  CCTGACACAG GTGAGCGAGG CAGCCGGGCC CCTTGTCCCA CCACCCGCAC
1351  TTCCCAACTG CACAGCCTCG AGTAGAACCC TGGATCCGGC TTGTTAAAGG
1401  ACCAAAGGGC ATCTAACAGC TTCTAGACAG TGTGGCCCGA GGATCCCTGG
1451  GGGTTATGCT TGAACGTTAC AGGGTTGAGG CTAAAGACTG AGGATTGATT
1501  GTAGGGAACC TCCAGTTATT AAACGGTGCG GATTGCTAGA GGGTGGCATA
1551  GTCCTTCAAT CCTGGCACCC GAAAAGCAGA TGCAGGAGCA GGAGCAGGAG
1601  CAAAGCCAGC CATGGAGTTT GAGGCCTGCT TGAACTACCT GAGATCCAAT
1651  AATAAAACAT TTCATATGCT GTGAAAAAAA AAAAAAAAA
```

FIGURE 1

```
1     ATG AAT GGC TCC GGC AGC CAG GGC GCG GAG AAC ACG AGC CAG GAA GGC GGT AGC GGC GGC
1     Met Asn Gly Ser Gly Ser Gln Gly Ala Glu Asn Thr Ser Gln Glu Gly Gly Ser Gly Gly

61    TGG CAG CCT GAG GCG GTC CTT GTA CCC CTA TTT TTC GCG CTC ATC TTC CTC GTG GGC ACC
21    Trp Gln Pro Glu Ala Val Leu Val Pro Leu Phe Phe Ala Leu Ile Phe Leu Val Gly Thr

121   GTG GGC AAC GCG CTG GTG CTG GCG GTG CTG CTG CGC GGC GGC CAG GCG GTC AGC ACC ACC
41    Val Gly Asn Ala Leu Val Leu Ala Val Leu Leu Arg Gly Gly Gln Ala Val Ser Thr Thr

181   AAC CTG TTC ATC CTC AAC CTG GGC GTG GCC GAC CTG TGT TTC ATC CTG TGC TGC GTG CCT
61    Asn Leu Phe Ile Leu Asn Leu Gly Val Ala Asp Leu Cys Phe Ile Leu Cys Cys Val Pro

241   TTC CAG GCC ACC ATC TAC ACC CTG GAC GAC TGG GTG TTC GGC TCG CTG CTC TGC AAG GCT
81    Phe Gln Ala Thr Ile Tyr Thr Leu Asp Asp Trp Val Phe Gly Ser Leu Leu Cys Lys Ala

301   GTT CAT TTC CTC ATC TTT CTC ACT ATG CAC GCC AGC AGC TTC ACG CTG GCC GCC GTC TCC
101   Val His Phe Leu Ile Phe Leu Thr Met His Ala Ser Ser Phe Thr Leu Ala Ala Val Ser

361   CTG GAC AGG TAT CTG GCC ATC CGC TAC CCG CTG CAC TCC CGA GAG TTG CGC ACA CCT CGA
121   Leu Asp Arg Tyr Leu Ala Ile Arg Tyr Pro Leu His Ser Arg Glu Leu Arg Thr Pro Arg

421   AAC GCG CTG GCC GCC ATC GGG CTC ATC TGG GGG CTA GCA CTG CTC TTC TCC GGG CCC TAC
141   Asn Ala Leu Ala Ala Ile Gly Leu Ile Trp Gly Leu Ala Leu Leu Phe Ser Gly Pro Tyr

481   CTG AGC TAC TAC CGT CAG TCG CAG CTG GCC AAC CTG ACA GTA TGC CAC CCA GCA TGG AGC
161   Leu Ser Tyr Tyr Arg Gln Ser Gln Leu Ala Asn Leu Thr Val Cys His Pro Ala Trp Ser

541   GCA CCT CGA CGT CGA GCC ATG GAC CTC TGC ACC TTC GTC TTT AGC TAC CTG CTG CCA GTG
181   Ala Pro Arg Arg Arg Ala Met Asp Leu Cys Thr Phe Val Phe Ser Tyr Leu Leu Pro Val

601   CTA GTC CTC AGT CTG ACC TAT GCG CGT ACC CTG CGC TAC CTC TGG CGC ACA GTC GAC CCG
201   Leu Val Leu Ser Leu Thr Tyr Ala Arg Thr Leu Arg Tyr Leu Trp Arg Thr Val Asp Pro

661   GTG ACT GCA GGC TCA GGT TCC CAG AGC GCC AAA CGC AAG GTG ACA CGG ATG ATC ATC ATC
221   Val Thr Ala Gly Ser Gly Ser Gln Ser Ala Lys Arg Lys Val Thr Arg Met Ile Ile Ile

721   GTG GCG GTG CTT TTC TGC CTC TGT TGG ATG CCC CAC CAC GCG CTT ATC CTC TGC GTG TGG
241   Val Ala Val Leu Phe Cys Leu Cys Trp Met Pro His His Ala Leu Ile Leu Cys Val Trp

781   TTT GGT CGC TTC CCG CTC ACG CGT GCC ACT TAC GCG TTG CGC ATC CTT TCA CAC CTA GTT
261   Phe Gly Arg Phe Pro Leu Thr Arg Ala Thr Tyr Ala Leu Arg Ile Leu Ser His Leu Val

841   TCC TAT GCC AAC TCC TGT GTC AAC CCC ATC GTT TAC GCT CTG GTC TCC AAG CAT TTC CGT
281   Ser Tyr Ala Asn Ser Cys Val Asn Pro Ile Val Tyr Ala Leu Val Ser Lys His Phe Arg

901   AAA GGT TTC CGC AAA ATC TGC GCG GGC CTG CTG CGC CCT GCC CCG AGG CGA GCT TCG GGC
301   Lys Gly Phe Arg Lys Ile Cys Ala Gly Leu Leu Arg Pro Ala Pro Arg Arg Ala Ser Gly

961   CGA GTG AGC ATC CTG GCG CCT GGG AAC CAT AGT GGC AGC ATG CTG GAA CAG GAA TCC ACA
321   Arg Val Ser Ile Leu Ala Pro Gly Asn His Ser Gly Ser Met Leu Glu Gln Glu Ser Thr

1021  GAC CTG ACA CAG GTG AGC GAG GCA GCC GGG CCC CTT GTC CCA CCA CCC GCA CTT CCC AAC
341   Asp Leu Thr Gln Val Ser Glu Ala Ala Gly Pro Leu Val Pro Pro Pro Ala Leu Pro Asn

1081  TGC ACA GCC TCG AGT AGA ACC CTG GAT CCG GCT TGT TAA    1119
361   Cys Thr Ala Ser Ser Arg Thr Leu Asp Pro Ala Cys  *     372
```

FIGURE 2

```
   1 CCACTTTGGT GATACCATGA ATGGCTCCGG CAGCCAGGGC GCGGAGAACA
  51 CGAGCCAGGA AGGCGGTAGC GGCGGCTGGC AGCCTGAGGC GGTCCTTGTA
 101 CCCCTATTTT TCGCGCTCAT CTTCCTCGTG GGCACCGTGG GCAACGCGCT
 151 GGTGCTGGCG GTGCTGCTGC GCGGCGGCCA GGCGGTCAGC ACCACCAACC
 201 TGTTCATCCT CAACCTGGGC GTGGCCGACC TGTGTTTCAT CCTGTGCTGC
 251 GTGCCTTTCC AGGCCACCAT CTACACCCTG GACGACTGGG TGTTCGGCTC
 301 GCTGCTCTGC AAGGCTGTTC ATTTCCTCAT CTTTCTCACT ATGCACGCCA
 351 GCAGCTTCAC GCTGGCCGCC GTCTCCCTGG ACAGGTAAAG GACCCAGAAA
 401 GAAACATCCA GTATGCCCGG AGGGATCTTG ACTGGAAAAG ACTGAATCCT
 451 GGTCTGGTGA CCTTAGTTCC CTGCCCTTTC ACATCACTTG GACATTCCCA
 501 CAGAAGAGCG GTGAAGAGGC GGTGGTCCTT ATTCTCCTCT GGTTTCCACT
 551 GAGTGCAACA TGTGCGTCCT GAGTACGCTG GAGGGACTCA CAAAATTTCA
 601 GCTTTCTTTA GGAGTTTCCT TGCTGTAGTT TGACCCAAGT CTTCTCCAGG
 651 TTTCTGTCAG AACTCAGGCA TGAGGGATCT GCCTCCCCTG GTTGTCACCA
 701 GAGGATAACA ATCACTGCCC CCAGAAATCC AGACAGATTC TACAACTTTT
 751 AGTCTTCGGT GTTTTGGGGG TGCCCCTTCA CGTGGAGTAG GTCGGTGGCC
 801 ACATTCCCAG GAGTGACAAT AGCCTAGCAG TGAATCCTCT CGCTTAGCTG
 851 ATGCCCCCCC ACTGTCCCCA CAGGTATCTG GCCATCCGCT ACCCGCTGCA
 901 CTCCCGAGAG TTGCGCACAC CTCGAAACGC GCTGGCCGCC ATCGGGCTCA
 951 TCTGGGGGCT AGCACTGCTC TTCTCCGGGC CCTACCTGAG CTACTACCGT
1001 CAGTCGCAGC TGGCCAACCT GACAGTATGC CACCCAGCAT GGAGCGCACC
1051 TCGACGTCGA GCCATGGACC TCTGCACCTT CGTCTTTAGC TACCTGCTGC
1101 CAGTGCTAGT CCTCAGTCTG ACCTATGCGC GTACCCTGCG CTACCTCTGG
1151 CGCACAGTCG ACCCGGTGAC TGCAGGCTCA GGTTCCCAGC GCGCCAAACG
1201 CAAGGTGACA CGGATGATCA TCATCGTGGC GGTGCTTTTC TGCCTCTGTT
1251 GGATGCCCCA CCACGCGCTT ATCCTCTGCG TGTGGTTTGG TCGCTTCCCG
1301 CTCACGCGTG CCACTTACGC GTTGCGCATC CTTTCACACC TAGTTTCCTA
1351 TGCCAACTCC TGTGTCAACC CCATCGTTTA CGCTCTGGTC TCCAAGCATT
1401 TCCGTAAAGG TTTCCGCAAA ATCTGCGCGG GCCTGCTGCG CCCTGCCCCG
1451 AGGCGAGCTT CGGGCCGAGT GAGCATCCTG GCGCCTGGGA ACCATAGTGG
1501 CAGCATGCTG GAACAGGAAT CCACAGACCT GACACAGGTG AGCGAGGCAG
1551 CCGGGCCCCT TGTCCCACCA CCCGCACTTC CCAACTGCAC AGCCTCGAGT
1601 AGAACCCTGG ATCCGGCTTG TTAAAGGACC AAAGGGCATC TAACAGCTTC
```

FIGURE 3

```
1651  TAGACAGTGT GGCCCGAGGA TCCCTGGGGG TTATGCTTGA ACGTTACAGG

1701  GTTGAGGCTA AAGACTGAGG ATTGATTGTA GGGAACCTCC AGTTATTAAA

1751  CGGTGCGGAT TGCTAGAGGG TGGCATAGTC CTTCAATCCT GGCACCCGAA

1801  AAGCAGATGC AGGAGCAGGA GCAGGAGCAA AGCCAGCCAT GGAGTTTGAG

1851  GCCTGCTTGA ACTACCTGAG ATCCAATAAT AAAACATTTC ATATGCTGTG

1901  AAAAAAAAAA AAAAAAAAAA AAAAAAAAAA AAAAAAAAAA AAAAAAAAAA

1951  AAAAAAAA
```

FIGURE 4

```
1     ATG AAT GGC TCC GGC AGC CAG GGC GCG GAG AAC ACG AGC CAG GAA GGC GGT AGC GGC GGC
1     Met Asn Gly Ser Gly Ser Gln Gly Ala Glu Asn Thr Ser Gln Glu Gly Gly Ser Gly Gly

61    TGG CAG CCT GAG GCG GTC CTT GTA CCC CTA TTT TTC GCG CTC ATC TTC CTC GTG GGC ACC
21    Trp Gln Pro Glu Ala Val Leu Val Pro Leu Phe Phe Ala Leu Ile Phe Leu Val Gly Thr

121   GTG GGC AAC GCG CTG GTG CTG GCG GTG CTG CTG CGC GGC GGC CAG GCG GTC AGC ACC ACC
41    Val Gly Asn Ala Leu Val Leu Ala Val Leu Leu Arg Gly Gly Gln Ala Val Ser Thr Thr

181   AAC CTG TTC ATC CTC AAC CTG GGC GTG GCC GAC CTG TGT TTC ATC CTG TGC TGC GTG CCT
61    Asn Leu Phe Ile Leu Asn Leu Gly Val Ala Asp Leu Cys Phe Ile Leu Cys Cys Val Pro

241   TTC CAG GCC ACC ATC TAC ACC CTG GAC GAC TGG GTG TTC GGC TCG CTG CTC TGC AAG GCT
81    Phe Gln Ala Thr Ile Tyr Thr Leu Asp Asp Trp Val Phe Gly Ser Leu Leu Cys Lys Ala

301   GTT CAT TTC CTC ATC TTT CTC ACT ATG CAC GCC AGC AGC TTC ACG CTG GCC GCC GTC TCC
101   Val His Phe Leu Ile Phe Leu Thr Met His Ala Ser Ser Phe Thr Leu Ala Ala Val Ser

361   CTG GAC AGG TAT CTG GCC ATC CGC TAC CCG CTG CAC TCC CGA GAG TTG CGC ACA CCT CGA
121   Leu Asp Arg Tyr Leu Ala Ile Arg Tyr Pro Leu His Ser Arg Glu Leu Arg Thr Pro Arg

421   AAC GCG CTG GCC GCC ATC GGG CTC ATC TGG GGG CTA GCA CTG CTC TTC TCC GGG CCC TAC
141   Asn Ala Leu Ala Ala Ile Gly Leu Ile Trp Gly Leu Ala Leu Leu Phe Ser Gly Pro Tyr

481   CTG AGC TAC TAC CGT CAG TCG CAG CTG GCC AAC CTG ACA GTA TGC CAC CCA GCA TGG AGC
161   Leu Ser Tyr Tyr Arg Gln Ser Gln Leu Ala Asn Leu Thr Val Cys His Pro Ala Trp Ser

541   GCA CCT CGA CGT CGA GCC ATG GAC CTC TGC ACC TTC GTC TTT AGC TAC CTG CTG CCA GTG
181   Ala Pro Arg Arg Arg Ala Met Asp Leu Cys Thr Phe Val Phe Ser Tyr Leu Leu Pro Val

601   CTA GTC CTC AGT CTG ACC TAT GCG CGT ACC CTG CGC TAC CTC TGG CGC ACA GTC GAC CCG
201   Leu Val Leu Ser Leu Thr Tyr Ala Arg Thr Leu Arg Tyr Leu Trp Arg Thr Val Asp Pro

661   GTG ACT GCA GGC TCA GGT TCC CAG CGC GCC AAA CGC AAG GTG ACA CGG ATG ATC ATC ATC
221   Val Thr Ala Gly Ser Gly Ser Gln Arg Ala Lys Arg Lys Val Thr Arg Met Ile Ile Ile

721   GTG GCG GTG CTT TTC TGC CTC TGT TGG ATG CCC CAC CAC GCG CTT ATC CTC TGC GTG TGG
241   Val Ala Val Leu Phe Cys Leu Cys Trp Met Pro His His Ala Leu Ile Leu Cys Val Trp

781   TTT GGT CGC TTC CCG CTC ACG CGT GCC ACT TAC GCG TTG CGC ATC CTT TCA CAC CTA GTT
261   Phe Gly Arg Phe Pro Leu Thr Arg Ala Thr Tyr Ala Leu Arg Ile Leu Ser His Leu Val

841   TCC TAT GCC AAC TCC TGT GTC AAC CCC ATC GTT TAC GCT CTG GTC TCC AAG CAT TTC CGT
281   Ser Tyr Ala Asn Ser Cys Val Asn Pro Ile Val Tyr Ala Leu Val Ser Lys His Phe Arg

901   AAA GGT TTC CGC AAA ATC TGC GCG GGC CTG CTG CGC CCT GCC CCG AGG CGA GCT TCG GGC
301   Lys Gly Phe Arg Lys Ile Cys Ala Gly Leu Leu Arg Pro Ala Pro Arg Arg Ala Ser Gly

961   CGA GTG AGC ATC CTG GCG CCT GGG AAC CAT AGT GGC AGC ATG CTG GAA CAG GAA TCC ACA
321   Arg Val Ser Ile Leu Ala Pro Gly Asn His Ser Gly Ser Met Leu Glu Gln Glu Ser Thr

1021  GAC CTG ACA CAG GTG AGC GAG GCA GCC GGG CCC CTT GTC CCA CCA CCC GCA CTT CCC AAC
341   Asp Leu Thr Gln Val Ser Glu Ala Ala Gly Pro Leu Val Pro Pro Pro Ala Leu Pro Asn

1081  TGC ACA GCC TCG AGT AGA ACC CTG GAT CCG GCT TGT TAA  1119
361   Cys Thr Ala Ser Ser Arg Thr Leu Asp Pro Ala Cys  *   372
```

FIGURE 5

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1690
      (B) TYPE:   Nucleic Acid
      (C) STRANDEDNESS: Single
      (D) TOPOLOGY: Linear    (vii) IMMEDIATE SOURCE:
      (B) CLONE:  Clone BMB77 nucleic acid sequence    (xi) SEQUENCE DESCRIPTION:  SEQ ID NO: 1:

```
TCGACCCACG CGTCCGCTCA AGTCTAAAGC AGAGCGAGTC CCAGGACTTG AGCGCGGGAA     60

GCGAATGGAG TCAGGGTCAT TCGATTGCAC CTCTCTCGGC TGCGGGCCGG AGCGGGGTAC    120

CATCCTACAC TCTGGGTGCT CCCTCCTCCT CCCGTCCCCC GCGCACCCCT GCCCTGGCTC    180

CTGGAGCTCG GCAGTCTCGC TGGGGCGCTG CAGCGAGGGA GCAGCGTGCT CACCAAGACC    240

CGGACAGCTG CGGGAGCGGC GTCCACTTTG GTGATACCAT GAATGGCTCC GGCAGCCAGG    300

GCGCGGAGAA CACGAGCCAG GAAGGCGGTA GCGGCGGCTG GCAGCCTGAG GCGGTCCTTG    360

TACCCCTATT TTTCGCGCTC ATCTTCCTCG TGGGCACCGT GGGCAACGCG CTGGTGCTGG    420

CGGTGCTGCT GCGCGGCGGC CAGGCGGTCA GCACCACCAA CCTGTTCATC CTCAACCTGG    480

GCGTGGCCGA CCTGTGTTTC ATCCTGTGCT GCGTGCCTTT CCAGGCCACC ATCTACACCC    540

TGGACGACTG GGTGTTCGGC TCGCTGCTCT GCAAGGCTGT TCATTTCCTC ATCTTTCTCA    600

CTATGCACGC CAGCAGCTTC ACGCTGGCCG CCGTCTCCCT GGACAGGTAT CTGGCCATCC    660

GCTACCCGCT GCACTCCCGA GAGTTGCGCA CACCTCGAAA CGCGCTGGCC GCCATCGGGC    720

TCATCTGGGG GCTAGCACTG CTCTTCTCCG GGCCCTACCT GAGCTACTAC CGTCAGTCGC    780

AGCTGGCCAA CCTGACAGTA TGCCACCCAG CATGGAGCGC ACCTCGACGT CGAGCCATGG    840

ACCTCTGCAC CTTCGTCTTT AGCTACCTGC TGCCAGTGCT AGTCCTCAGT CTGACCTATG    900

CGCGTACCCT GCGCTACCTC TGGCGCACAG TCGACCCGGT GACTGCAGGC TCAGGTTCCC    960

AGAGCGCCAA ACGCAAGGTG ACACGGATGA TCATCATCGT GGCGGTGCTT TTCTGCCTCT   1020

GTTGGATGCC CCACCACGCG CTTATCCTCT GCGTGTGGTT TGGTCGCTTC CCGCTCACGC   1080

GTGCCACTTA CGCGTTGCGC ATCCTTTCAC ACCTAGTTTC CTATGCCAAC TCCTGTGTCA   1140

ACCCCATCGT TTACGCTCTG GTCTCCAAGC ATTTCCGTAA AGGTTTCCGC AAAATCTGCG   1200

CGGGCCTGCT GCGCCCTGCC CCGAGGCGAG CTTCGGGCCG AGTGAGCATC CTGGCGCCTG   1260

GGAACCATAG TGGCAGCATG CTGGAACAGG AATCCACAGA CCTGACACAG GTGAGCGAGG   1320

CAGCCGGGCC CCTTGTCCCA CCACCCGCAC TTCCCAACTG CACAGCCTCG AGTAGAACCC   1380

TGGATCCGGC TTGTTAAAGG ACCAAAGGGC ATCAACAGC TTCTAGACAG TGTGGCCCGA    1440

GGATCCCTGG GGGTTATGCT TGAACGTTAC AGGGTTGAGG CTAAAGACTG AGGATTGATT   1500

GTAGGGAACC TCCAGTTATT AAACGGTGCG GATTGCTAGA GGGTGGCATA GTCCTTCAAT   1560

CCTGGCACCC GAAAAGCAGA TGCAGGAGCA GGAGCAGGAG CAAAGCCAGC CATGGAGTTT   1620

GAGGCCTGCT TGAACTACCT GAGATCCAAT AATAAAACAT TCATATGCT GTGAAAAAAA    1680

AAAAAAAAA                                                          1690
```

(2) INFORMATION FOR SEQ ID NO:2:

(i) SEQUENCE CHARACTERISTICS:
        (A) LENGTH: 372
        (B) TYPE: Amino Acid Sequence
        (C) STRANDEDNESS: Single
        (D) TOPOLOGY: Linear     (vii) IMMEDIATE SOURCE:
        (B) CLONE: Clone BMB77 amino acid sequence     (xi) SEQUENCE DESCRIPTION: SEQ ID NO: 2:

```
Met Asn Gly Ser Gly Ser Gln Gly Ala Glu Asn Thr Ser Gln Glu
1               5                   10                  15

Gly Gly Ser Gly Gly Trp Gln Pro Glu Ala Val Leu Val Pro Leu
            20                  25                  30

Phe Phe Ala Leu Ile Phe Leu Val Gly Thr Val Gly Asn Ala Leu
            35                  40                  45

Val Leu Ala Val Leu Leu Arg Gly Gly Gln Ala Val Ser Thr Thr
50                  55                  60

Asn Leu Phe Ile Leu Asn Leu Gly Val Ala Asp Leu Cys Phe Ile
65                  70                  75

Leu Cys Cys Val Pro Phe Gln Ala Thr Ile Tyr Thr Leu Asp Asp
            80                  85                  90

Trp Val Phe Gly Ser Leu Leu Cys Lys Ala Val His Phe Leu Ile
            95                  100                 105

Phe Leu Thr Met His Ala Ser Ser Phe Thr Leu Ala Ala Val Ser
            110                 115                 120

Leu Asp Arg Tyr Leu Ala Ile Arg Tyr Pro Leu His Ser Arg Glu
            125                 130                 135

Leu Arg Thr Pro Arg Asn Ala Leu Ala Ala Ile Gly Leu Ile Trp
140                 145                 150

Gly Leu Ala Leu Leu Phe Ser Gly Pro Tyr Leu Ser Tyr Tyr Arg
            155                 160                 165

Gln Ser Gln Leu Ala Asn Leu Thr Val Cys His Pro Ala Trp Ser
            170                 175                 180

Ala Pro Arg Arg Arg Ala Met Asp Leu Cys Thr Phe Val Phe Ser
            185                 190                 195

Tyr Leu Leu Pro Val Leu Val Leu Ser Leu Thr Tyr Ala Arg Thr
200                 205                 210

Leu Arg Tyr Leu Trp Arg Thr Val Asp Pro Val Thr Ala Gly Ser
            215                 220                 225

Gly Ser Gln Ser Ala Lys Arg Lys Val Thr Arg Met Ile Ile Ile
            230                 235                 240

Val Ala Val Leu Phe Cys Leu Cys Trp Met Pro His His Ala Leu
            245                 250                 255

Ile Leu Cys Val Trp Phe Gly Arg Phe Pro Leu Thr Arg Ala Thr
260                 265                 270

Tyr Ala Leu Arg Ile Leu Ser His Leu Val Ser Tyr Ala Asn Ser
275                 280                 285

Cys Val Asn Pro Ile Val Tyr Ala Leu Val Ser Lys His Phe Arg
            290                 295                 300

Lys Gly Phe Arg Lys Ile Cys Ala Gly Leu Leu Arg Pro Ala Pro
            305                 310                 315

Arg Arg Ala Ser Gly Arg Val Ser Ile Leu Ala Pro Gly Asn His
320                 325                 330
```

```
Ser Gly Ser Met Leu Glu Gln Glu Ser Thr Asp Leu Thr Gln Val
    335                 340                 345

Ser Glu Ala Ala Gly Pro Leu Val Pro Pro Ala Leu Pro Asn
350                 355                 360

Cys Thr Ala Ser Ser Arg Thr Leu Asp Pro Ala Cys
                365                 370

(2) INFORMATION FOR SEQ ID NO:3:

(i) SEQUENCE CHARACTERISTICS:
        (A) LENGTH: 1958
        (B) TYPE: Nucleic Acid
        (C) STRANDEDNESS: Single
        (D) TOPOLOGY: Linear (vii) IMMEDIATE SOURCE:
        (B) CLONE: Clone Y107 nucleic acid sequence (xi) SEQUENCE DESCRIPTION: SEQ ID NO: 3:

CCACTTTGGT GATACCATGA ATGGCTCCGG CAGCCAGGGC GCGGAGAACA CGAGCCAGGA     60

AGGCGGTAGC GGCGGCTGGC AGCCTGAGGC GGTCCTTGTA CCCCTATTTT TCGCGCTCAT    120

CTTCCTCGTG GGCACCGTGG GCAACGCGCT GGTGCTGGCG GTGCTGCTGC GCGGCGGCCA    180

GGCGGTCAGC ACCACCAACC TGTTCATCCT CAACCTGGGC GTGGCCGACC TGTGTTTCAT    240

CCTGTGCTGC GTGCCTTTCC AGGCCACCAT CTACACCCTG GACGACTGGG TGTTCGGCTC    300

GCTGCTCTGC AAGGCTGTTC ATTTCCTCAT CTTTCTCACT ATGCACGCCA GCAGCTTCAC    360

GCTGGCCGCC GTCTCCCTGG ACAGGTAAAG GACCCAGAAA GAAACATCCA GTATGCCCGG    420

AGGGATCTTG ACTGGAAAAG ACTGAATCCT GGTCTGGTGA CCTTAGTTCC CTGCCCTTTC    480

ACATCACTTG ACATTCCCA CAGAAGAGCG GTGAAGAGGC GGTGGTCCTT ATTCTCCTCT     540

GGTTTCCACT GAGTGCAACA TGTGCGTCCT GAGTACGCTG GAGGGACTCA CAAAATTTCA    600

GCTTTCTTTA GGAGTTTCCT TGCTGTAGTT TGACCCAAGT CTTCTCCAGG TTTCTGTCAG    660

AACTCAGGCA TGAGGGATCT GCCTCCCCTG GTTGTCACCA GAGGATAACA ATCACTGCCC    720

CCAGAAATCC AGACAGATTC TACAACTTTT AGTCTTCGGT GTTTTGGGGG TGCCCCTTCA    780

CGTGGAGTAG GTCGGTGGCC ACATTCCCAG GAGTGACAAT AGCCTAGCAG TGAATCCTCT    840

CGCTTAGCTG ATGCCCCCCC ACTGTCCCCA CAGGTATCTG GCCATCCGCT ACCCGCTGCA    900

CTCCCGAGAG TTGCGCACAC CTCGAAACGC GCTGGCCGCC ATCGGGCTCA TCTGGGGGCT    960

AGCACTGCTC TTCTCCGGGC CCTACCTGAG CTACTACCGT CAGTCGCAGC TGGCCAACCT   1020

GACAGTATGC CACCCAGCAT GGAGCGCACC TCGACGTCGA GCCATGGACC TCTGCACCTT   1080

CGTCTTTAGC TACCTGCTGC CAGTGCTAGT CCTCAGTCTG ACCTATGCGC GTACCCTGCG   1140

CTACCTCTGG CGCACAGTCG ACCCGGTGAC TGCAGGCTCA GGTTCCCAGC GCGCCAAACG   1200

CAAGGTGACA CGGATGATCA TCATCGTGGC GGTGCTTTTC TGCCTCTGTT GGATGCCCCA   1260

CCACGCGCTT ATCCTCTGCG TGTGGTTTGG TCGCTTCCCG CTCACGCGTG CCACTTACGC   1320

GTTGCGCATC CTTTCACACC TAGTTTCCTA TGCCAACTCC TGTGTCAACC CCATCGTTTA   1380

CGCTCTGGTC TCCAAGCATT TCCGTAAAGG TTTCCGCAAA ATCTGCGCGG GCCTGCTGCG   1440

CCCTGCCCCG AGGCGAGCTT CGGGCCGAGT GAGCATCCTG GCGCCTGGGA ACCATAGTGG   1500

CAGCATGCTG GAACAGGAAT CCACAGACCT GACACAGGTG AGCGAGGCAG CCGGGCCCCT   1560

TGTCCCACCA CCCGCACTTC CCAACTGCAC AGCCTCGAGT AGAACCCTGG ATCCGGCTTG   1620

TTAAAGGACC AAAGGGCATC TAACAGCTTC TAGACAGTGT GGCCCGAGGA TCCCTGGGGG   1680
```

```
TTATGCTTGA ACGTTACAGG GTTGAGGCTA AAGACTGAGG ATTGATTGTA GGGAACCTCC      1740

AGTTATTAAA CGGTGCGGAT TGCTAGAGGG TGGCATAGTC CTTCAATCCT GGCACCCGAA      1800

AAGCAGATGC AGGAGCAGGA GCAGGAGCAA AGCCAGCCAT GGAGTTTGAG GCCTGCTTGA      1860

ACTACCTGAG ATCCAATAAT AAAACATTTC ATATGCTGTG AAAAAAAAAA AAAAAAAAA      1920

AAAAAAAAAA AAAAAAAAAA AAAAAAAAAA AAAAAAA                             1958

(2) INFORMATION FOR SEQ ID NO:4:

(i) SEQUENCE CHARACTERISTICS:
        (A) LENGTH: 372
        (B) TYPE: Amino Acid Sequence
        (C) STRANDEDNESS: Single
        (D) TOPOLOGY: Linear (vii) IMMEDIATE SOURCE:
        (B) CLONE: Clone Y107 amino acid sequence
            (omitting putative intron)

(xi) SEQUENCE DESCRIPTION: SEQ ID NO: 4:
```

Met Asn Gly Ser Gly Ser Gln Gly Ala Glu Asn Thr Ser Gln Glu
1               5                   10                  15

Gly Gly Ser Gly Gly Trp Gln Pro Glu Ala Val Leu Val Pro Leu
            20                  25                  30

Phe Phe Ala Leu Ile Phe Leu Val Gly Thr Val Gly Asn Ala Leu
        35                  40                  45

Val Leu Ala Val Leu Leu Arg Gly Gly Gln Ala Val Ser Thr Thr
    50                  55                  60

Asn Leu Phe Ile Leu Asn Leu Gly Val Ala Asp Leu Cys Phe Ile
65                  70                  75

Leu Cys Cys Val Pro Phe Gln Ala Thr Ile Tyr Thr Leu Asp Asp
                80                  85                  90

Trp Val Phe Gly Ser Leu Leu Cys Lys Ala Val His Phe Leu Ile
                    95                  100                 105

Phe Leu Thr Met His Ala Ser Ser Phe Thr Leu Ala Ala Val Ser
                110                 115                 120

Leu Asp Arg Tyr Leu Ala Ile Arg Tyr Pro Leu His Ser Arg Glu
        125                 130                 135

Leu Arg Thr Pro Arg Asn Ala Leu Ala Ala Ile Gly Leu Ile Trp
140                 145                 150

Gly Leu Ala Leu Leu Phe Ser Gly Pro Tyr Leu Ser Tyr Tyr Arg
                155                 160                 165

Gln Ser Gln Leu Ala Asn Leu Thr Val Cys His Pro Ala Trp Ser
            170                 175                 180

Ala Pro Arg Arg Arg Ala Met Asp Leu Cys Thr Phe Val Phe Ser
            185                 190                 195

Tyr Leu Leu Pro Val Leu Val Leu Ser Leu Thr Tyr Ala Arg Thr
        200                 205                 210

Leu Arg Tyr Leu Trp Arg Thr Val Asp Pro Val Thr Ala Gly Ser
215                 220                 225

Gly Ser Gln Arg Ala Lys Arg Lys Val Thr Arg Met Ile Ile Ile
            230                 235                 240

Val Ala Val Leu Phe Cys Leu Cys Trp Met Pro His His Ala Leu
                245                 250                 255

Ile Leu Cys Val Trp Phe Gly Arg Phe Pro Leu Thr Arg Ala Thr
                260                 265                 270

-continued

```
Tyr Ala Leu Arg Ile Leu Ser His Leu Val Ser Tyr Ala Asn Ser
    275                 280                 285

Cys Val Asn Pro Ile Val Tyr Ala Leu Val Ser Lys His Phe Arg
290                 295                 300

Lys Gly Phe Arg Lys Ile Cys Ala Gly Leu Leu Arg Pro Ala Pro
                305                 310                 315

Arg Arg Ala Ser Gly Arg Val Ser Ile Leu Ala Pro Gly Asn His
            320                 325                 330

Ser Gly Ser Met Leu Glu Gln Glu Ser Thr Asp Leu Thr Gln Val
        335                 340                 345

Ser Glu Ala Ala Gly Pro Leu Val Pro Pro Pro Ala Leu Pro Asn
    350                 355                 360

Cys Thr Ala Ser Ser Arg Thr Leu Asp Pro Ala Cys
365                 370
```

GALANIN RECEPTOR 2 PROTEIN

BACKGROUND OF THE INVENTION

1. Field of the Invention

This invention relates to a novel neuropeptide galanin receptor and its nucleic acid sequence.

2. Description of the Related Art

Galanin is a 29 amino acid peptide hormone (30 amino acids in human) which is present in a wide range of central and peripheral tissues. Skofitsch, *Peptides* 6, 509 (1985); Merchenthaler, *Prog. Neurobiol.* 40, 711 (1993). Galanin is involved in many diverse physiological functions. Galanin is known to regulate the secretion of both endocrine and exocrine hormones. Galanin inhibits insulin secretion from pancreatic beta cells, and can inhibit pancreatic amylase secretion; in the stomach, galanin inhibits gastrin and somatostatin secretion. Galanin stimulates VIP (vasoactive intestinal protein) release from the hypothalamus, prolactin and growth hormone release from the pituitary; and inhibits the secretion of ACTH in the hypothalamus. Furthermore, the secretion of neurotransmitters can be modulated. For example, galanin can inhibit the release of histamine and norepinephrine in the hypothalamus. Other secondary messenger systems are also regulated: galanin can either stimulate or inhibit intracellular cAMP accumulation; is involved in the closure of N- and L-type voltage-sensitive calcium channels, and in the opening of ATP-sensitive and -insensitive potassium channels; and has been shown to stimulate the release of calcium from intracellular stores. Moreover, galanin is involved in the inhibition of acetylcholine release and the inhibition of muscarinic receptor-mediated phosphoinositide turnover. Bartfai, *Crit. Rev. Neurobiol.* 7, 229 (1993) Galanin is implicated in the modulation of many cognitive and sensory functions. Galanin has potent antinociceptive effects, and can impair performance in one-trial learning, t-maze, and swim maze learning and memory paradigms. Its inhibition of the anoxic release of glutamate, as well as its inhibitory actions on cholinergic function suggest a role in neuroprotection, and in the development of Alzheimer's Disease. Crawley, *Regulatory Peptides* 59, 1 (1995). Galanin is known to induce feeding in rodents and, in contrast with the effects of Neuropeptide Y on feeding, galanin increases preference for fat intake. Akabayashi, *Proc. Natl. Acad Sci. USA* 91, 10375 (1994). Galanin is also involved in the regulation of gastrointestinal smooth muscle contraction. Because of the important role of galanin in these many physiological processes, there is a strong need to further develop materials and methods for investigating the mechanistic behavior of the receptors and for treating diseased and other abnormal states associated with these physiological processes.

Pharmacological data suggest the existence of several galanin receptor subtypes. Wynick, *Proc. Natl. Acad Sci. USA* 90, 4231 (1990); Zen-Fa, *J. Pharmacol. Exp. Ther.* 272, 371 (1995). Galanin receptors are known to be linked to the $G_i$ proteins, and there is some evidence that certain galanin receptor subtypes may be linked to cholera toxin-sensitive $G_s$ proteins. Gillison, *Diabetes* 43, 24 (1994); Chen, *Am. J. Physiol.* 266, G113 (1994). One galanin receptor has been cloned and it is a member of the seven transmembrane (7TMD) class of G protein-linked receptors. It has been designated as GalR1. Habert-Ortoli, *Proc. Natl. Acad Sci. USA* 91, 9780; WO95/22608. In addition to this human GalR1 receptor, the GalR1 receptor has been obtained from rat Burgevin, *J. Mol. Neurosci.* 6, 33 (1995). The in vivo functions mediated through this cloned GalR1 receptor have not yet been elucidated. EP-0711830-A2 disclose a closely-related GalR1 sequence, differing in that Cys15→Trp is varied.

SUMMARY OF THE INVENTION

The present invention provides a novel galanin receptor protein, the GalR2 receptor. Also provided are the nucleic acid sequences encoding this novel receptor protein as well as methods for using this protein and its nucleic acid sequence, and methods useful for developing and identifying compounds for the treatment of diseases and disorders in which galanin is implicated. The importance of this discovery is manifested in the effects of galanin, which include antinociceptive activity, smooth muscle contraction, cardiovascular activity, pituitary hormone release, cognition, and increased food intake. Thus, this receptor protein is useful for screening for galanin agonist and antagonist activity for controlling these conditions.

In one aspect of the present invention, we provide isolated nucleic acid sequences for a novel galanin receptor, the GalR2 receptor. In particular, we provide the cDNA sequences encoding the rat receptor. These nucleic acid sequences have a variety of uses. For example, they are useful for making vectors and for transforming cells, both of which are ultimately useful for production of the GalR2 receptor protein. They are also useful as scientific research tools for developing nucleic acid probes for determining receptor expression levels, e.g. to identify diseased or otherwise abnormal states. They are useful for developing analytical tools such as antisense oligonucleotides for selectively inhibiting expression of the receptor gene to determine physiological responses. The present invention can also be used to isolate the homologous nucleic acid sequence of other species, such as human, primate, dog, mouse, etc.

In another aspect of the present invention, we provide a homogeneous composition comprising the receptor GalR2 protein. The protein is useful for screening drugs for agonist and antagonist activity, and, therefore, for screening for drugs useful in regulating physiological responses associated with the GalR2 receptor. Specifically, antagonists to the GalR2 receptor could be used to treat obesity and diabetes by reducing appetite and food consumption, whereas agonists could be used for the treatment of anorexic conditions. Furthermore, drugs could be used to treat Alzheimer's disease, stroke, neuropathic pain, and/or endocrine disorders. The proteins are also useful for developing antibodies for detection of the protein.

Flowing from the foregoing are a number of other aspects of the invention, including (a) vectors, such as plasmids, comprising the receptor GalR2 nucleic acid sequence that may further comprise additional regulatory elements, e.g, promotors, (b) transformed cells that express the GalR2 receptor, (c) nucleic acid probes, (d) antisense oligonucleotides, (e) agonists, (f) antagonists, and (g) transgenic mammals. Further aspects of the invention comprise methods for making and using the foregoing compounds and compositions.

The invention includes a polynucleotide molecule coding for human GalR2, or a galanin binding fragment thereof A polynucleotide molecule comprising SEQ ID NO:1 or a degenerate variant thereof. A purified and isolated human GalR2 protein. The GalR2 protein comprising SEQ ID NO:2. A purified and isolated human GalR2 protein or fragment thereof having GalR2 binding activity. A polynucleotide molecule coding for a variant of human GalR2 comprising SEQ ID NO:3, or a galanin binding fragment thereof. A polynucleotide molecule comprising SEQ ID NO:3 or a degenerate variant thereof. A purified and isolated variant of human GalR2 protein or fragment thereof having GalR2 binding activity. A purified and isolated variant of human GalR2 protein comprising SEQ ID NO:4.

The foregoing merely summarize certain aspects of the present invention and is not intended, nor should it be construed, to limit the invention in any manner. All patents and other publications recited herein are hereby incorporated by reference in their entirety.

BRIEF DESCRIPTION OF THE DRAWINGS

FIG. 1 is the polynucleotide sequence of human GalR2 of the invention.

FIG. 2 is the amino acid sequence of human GalR2.

FIGS. 3–4 are the polynucleotide sequence of the Y107 variant of human GalR2.

FIG. 5 is the amino acid sequence of Y107(omitting putative intron).

DETAILED DESCRIPTION OF THE PREFERRED EMBODIMENTS

Figure 4:
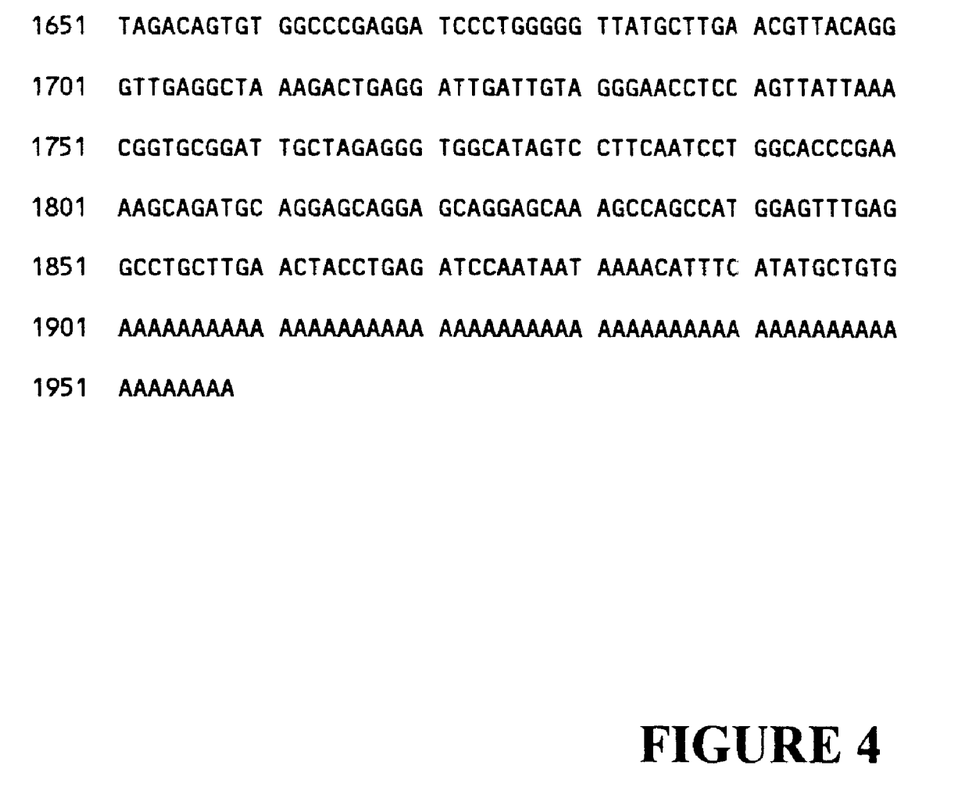

The present invention comprises, in part, a novel galanin receptor protein, the GalR2 receptor. Particularly preferred embodiments of the GalR2 receptor are those having an amino acid sequence substantially the same as SEQ ID NO: 2 or 4. As used herein, reference to the GalR2 receptor is meant as a reference to any protein having an amino acid sequence substantially the same as SEQ ID NO: 2 or 4. The present invention also comprises the nucleic acid sequence encoding the GalR2 protein, which nucleic acid sequences is substantially the same as SEQ ID NO: 1 or 3. Receptors SEQ ID NO: 1 and SEQ ID NO: 3 are nucleic acid sequences of rat GalR2 receptors but SEQ ID NO: 3 appears to contain an intronic region; therefore, SEQ ID NO: 1 is the preferred embodiment of the rat GalR2 receptor of this invention. Receptors SEQ ID NO: 2 and 4 are rat GalR2 receptors and appear to be allelic variants.

As used herein, a protein "having an amino acid sequence substantially the same as SEQ ID NO: x" (where "x" is the number of one of the protein sequences recited herein) means a protein whose amino acid sequence is the same as SEQ ID NO: x or differs only in a way such that $IC_{50}$ [galanin] as determined according to the method detailed in Example 2, infra, are less than or equal to 1 nM. Those skilled in the art will appreciate that conservative substitutions of amino acids can be made without significantly diminishing the protein's affinity for galanin and fragments and analogs thereof. Other substitutions may be made that increase the protein's affinity for these compounds. Making and identifying such proteins is a routine matter given the teachings herein, and can be accomplished, for example, by altering the nucleic acid sequence encoding the protein (as disclosed herein), inserting it into a vector, transforming a cell, expressing the nucleic acid sequence, and measuring the binding affinity of the resulting protein, all as taught herein.

As used herein the term "a molecule having a nucleotide sequence substantially the same as SEQ ID NO: y" (wherein "y" is the number of one of the protein-encoding nucleotide sequences listed in the Sequence Listing) means a nucleic acid encoding a protein "having an amino acid sequence substantially the same as SEQ ID NO: y*" (wherein "y*" is the number of the amino acid sequence for which nucleotide sequence "y" codes) as defined above. This definition is intended to encompass natural allelic variations in the GalR2 sequence. Cloned nucleic acid provided by the present invention may encode GalR2 protein of any species of origin, including (but not limited to), for example, mouse, rat, rabbit, cat, dog, primate, and human. Preferably the nucleic acid provided by the invention encodes GalR2 receptors of mammalian, and most preferably, rat or human origin.

The invention also includes nucleotide sequences encoding chimeric proteins comprised of parts of the GalR2 receptor and parts of other related seven-transmembrane receptors.

The BMB77 clone (SEQ ID NO: 1) (see Example 1, infra) has a 1.7-kb cDNA insert with a open reading frame from nucleotides 279 to 1394 that encodes a 372 amino acid protein (SEQ ID NO: 2). Hydrophobicity plot analysis using the PEPPLOT function of GCG (Genetics Computer Group, Madison, Wis.) shows that the GalR2 receptor has seven transmembrane-like domains, indicating it might be a G-protein-coupled receptor. GalR2 is 26 amino acids longer in length than GalR1, the only other published galanin receptor. This extra length of amino acids within GalR2 is due to an extended C-terminal tail sequence. However, the putative N-terminal extracellular domain of GalR2 is about 7 amino acids shorter than the corresponding region in GalR1. It is also important to note that the GalR2 sequence shows only 38% amino acid sequence identity to the GalR1 receptor.

The Y107 clone (SEQ ID NO: 3) (see Example 1, infra) has a 1.9-kb cDNA insert with an open reading frame from nucleotides 17–384, and from nucleotides 874–1621. The sequence between nucleotides 384 and 874 contains multiple STOP codons in all three reading frames. Furthermore, the dinucleotides GT and AG at positions 385–386 and 872–873, respectively, fulfill the criteria for being a splice donor and acceptor site, respectively. Moreover, when the nucleotide sequences 17–384 and 874–1621 are joined together, an open reading frame is formed which has a cognate translation product nearly identical to that of clone BMB77 (SEQ ID NO: 4). Therefore, it is likely that the region between these two open reading frames is an intron.

There is a single nucleotide change between positions 963 in clone BMB77 (SEQ ID NO: 1) and 1190 in clone Y107 (SEQ ID NO: 3). This adenine to cytosine transversion results in a change from $Ser^{229}$ in clone BMB77 (SEQ ID NO: 2) to $Arg^{229}$ in clone Y107 (SEQ ID NO: 4). Amino acid 229 is located in the third intracellular loop of GalR2. The third intracellular loop of other seven transmembrane domain G protein-coupled receptors is an important domain for effecting coupling of the receptor to its G protein. Bockaert, Curr. Op. Neurobiol. 1, 32–42 (1991). This polymorphic amino acid position could change the G protein binding characteristics of the GalR2 receptor variants. Gillison, Diabetes 43, 24 (1994); Chen, Am. J. Physiol. 266, G113 (1994).

Nucleic acid hybridization probes provided by the invention are DNAs consisting essentially of the nucleotide sequences complementary to any sequence depicted in SEQ ID NO:s 1 and 3 that is effective in nucleic acid hybridization. Nucleic acid probes are useful for detecting GalR2 gene expression in cells and tissues using techniques well-known in the art, including, but not limited to, Northern blot hybridization, in situ hybridization, and Southern hybridization to reverse transcriptase - polymerase chain reaction product DNAs. The probes provided by the present invention, including oligonucleotide probes derived therefrom, are also useful for Southern hybridization of mammalian, preferably human, genomic DNA for screening for restriction fragment length polymorphism (RFLP) associated with certain genetic disorders. As used herein, the term complementary means a nucleic acid having a sequence that is sufficiently complementary in the Watson-Crick sense to a target nucleic acid to bind to the target under physiological conditions or experimental conditions which those skilled in the art routinely use when employing probes.

Receptor GalR2 binds various fragments and analogs of galanin with affinities different from that of the known receptors. The rank order of binding affinity of receptor GalR2 was found to be:

galanin=(2-29)galanin>(1-15)galanin>>(3-29)galanin

Table 1, infra, presents a more detailed affinity profile of the GalR2 receptor for galanin and various fragments thereof. As used herein, a protein having substantially the same affinity profile as the GalR2 receptor means a protein in which the $IC_{50}$ of each of the peptides listed in Table 1, infra, is no more than an order of magnitude greater than those listed in Table 1 for each of the respective peptides as measured according to the methods described in Example 2.

The production of proteins such as receptor GalR2 from cloned genes by genetic engineering means is well known in this art. The discussion which follows is accordingly intended as an overview of this field, and is not intended to reflect the full state of the art.

DNA which encodes receptor GalR2 may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the GalR2 gene sequence information provided herein. Probes may be labeled with a detectable group such as a fluorescent group, a radioactive atom or a chemiluminescent group in accordance with known procedures and used in conventional hybridization assays, as described in greater detail in the Examples below. In the alternative, the GalR2 gene sequence may be obtained by use of the polymerase chain reaction (PCR) procedure, with the PCR oligonucleotide primers being produced from the GalR2 gene sequence provided herein. See U.S. Pat. No. 4,683,195 to Mullis et al. and U.S. Pat. No. 4,683,202 to Mullis.

Receptor GalR2 may be synthesized in host cells transformed with a recombinant expression construct comprising a nucleic acid encoding the receptor GalR2. Such a recombinant expression construct can also be comprised of a vector that is a replicable DNA construct. Vectors are used herein either to amplify DNA encoding GalR2 and/or to express DNA which encodes GalR2. For the purposes of this invention, a recombinant expression construct is a replicable DNA construct in which a DNA sequence encoding GalR2 is operably linked to suitable control sequences capable of effecting the expression of GalR2 in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., *Molecular Cloning: A Laboratory Manual* (2nd Edition, Cold Spring Harbor Press, New York, 1989).

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. The vectors may be self-replicating. Suitable vectors for the purposes of the present invention include pBluescript, pcDNA3, pSV-SPORT, and, for insect cells, baculovirus. A preferred vector is the plasmid pcDNA3 (Invitrogen, San Diego, Calif.).

Construction of suitable vectors containing the desired coding and control sequences employs standard ligation and restriction techniques that are well understood in the art. Isolated plasmids, DNA sequences, or synthesized oligonucleotides are cleaved, tailored, and relegated in the form desired.

Site-specific DNA cleavage is performed by treating with the suitable restriction enzyme (or enzymes) under conditions that are generally understood in the art, and the particulars of which are specified by the manufacturer of these commercially available restriction enzymes. See, e.g., *New England Biolabs, Product Catalog*. In general, about 1 μg of plasmid or DNA sequence is cleaved by one unit of enzyme in about 20 μl of buffer solution. Often excess of restriction enzyme is used to ensure complete digestion of the DNA substrate. Incubation times of about one hour to two hours at about 37° C. are workable, although variations are tolerable. After each incubation, protein is removed by extraction with phenol/chloroform, and may be followed by ether extraction. The nucleic acid may be recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* 65, 499–560 (1980).

Transformed host cells are cells which have been transformed or transfected with recombinant expression constructs made using recombinant DNA techniques and comprising mammalian GalR2-encoding sequences. Preferred host cells for transient transfection are COS-7 cells. Transformed host cells may ordinarily express GalR2, but host cells transformed for purposes of cloning or amplifying nucleic acid hybridization probe DNA need not express the receptor. When expressed, the mammalian GalR2 protein will typically be located in the host cell membrane. See, Sambrook et al., ibid.

Cultures of cells derived from multicellular organisms are desirable hosts for recombinant GalR2 protein synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See *Tissue Culture* (Academic Press, Kruse & Patterson, Eds., 1973). Examples of useful host cell lines are bacteria cells, insect cells, yeast cells, human 293 cells, VERO and HeLa cells, LMTK cells, and W1138, BHK, CHO, COS-7, CV, and MDCK cell lines (American Type Culture Collection, Rockville, Md.). CHO cells are preferred.

The invention provides homogeneous compositions of mammalian GalR2 produced by transformed eukaryotic cells as provided herein. Such homogeneous compositions are intended to be comprised of mammalian GalR2 protein that comprises at least 90% of the protein in such homogenous composition. The invention also provides membrane preparation from cells expressing GalR2 as the result of transformation with a recombinant expression construct, as described here.

Mammalian GalR2 protein made from cloned genes in accordance with the present invention may be used for screening compounds for GalR2 agonist or antagonist activity, or for determining the amount of a GalR2 agonist or antagonist drug in a solution (e.g., blood plasma or serum). For example, host cells may be transformed with a recombinant expression construct of the present invention, GalR2 protein expressed in those host cells, the cells lysed, and the membranes from those cells used to screen compounds for GalR2 binding activity. Competitive binding assays in which such procedures may be carried out are well known in the art. By selection of host cells which do not ordinarily express GalR2, pure or crude preparations of membranes containing GalR2 can be obtained. Further, GalR2 agonists and antagonists can be identified by transforming host cells with a recombinant expression construct as provided by the present invention. Membranes obtained from such cells (and membranes of intact cells) can be used in binding studies wherein the drug dissociation activity is monitored.

It is known that the neurotransmitter galanin is a regulator of appetite, cognition, endocrine function, pain, and smooth muscle control. As shown herein, the various galanin analogs/fragments that induce these physiological responses bind with a high affinity to the GalR2 receptor. It is therefore evident that by modulating the activity of the GalR receptor, various physiological activities can be regulated. Specifically, antagonists to the GalR2 receptor, identified by the methods described herein, could be used to treat obesity, diabetes, hyperlipidemia, stroke, neuropathic pain, Alzheimer's disease, and/or endocrine disorders.

This invention provides a pharmaceutical composition comprising an effective amount of a drug identified by the method described herein and a pharmaceutically acceptable carrier. Such drugs and carrier can be administered by various routes, for example oral, subcutaneous, intramuscular, intravenous or intracerebral. The preferred route of administration would be oral at daily doses of about 0.01–100 mg/kg.

This invention provides a method of treating obesity, diabetes, hyperlipidemia, stroke, neuropathic pain, Alzheimer's disease, or endocrine disorders wherein the abnormality is improved by reducing the activity of GalR2 receptor or blocking the binding of ligands to a GalR2 receptor which comprises administering an effective amount of the pharmaceutical composition described above.

The recombinant expression constructs of the present invention are useful in molecular biology to transform cells which do not ordinarily express GalR2 to thereafter express this receptor. Such cells are useful as intermediates for making cell membrane preparations useful for receptor binding assays, which are in turn useful for drug screening. Drugs identified from such receptor assays can be used for the treatment of obesity, diabetes, anorexia, hyperlipidemia stroke, neuropathic pain, Alzheimer's disease, or endocrine disorders.

The recombinant expression constructs of the present invention are also useful in gene therapy. Cloned genes of the present invention, or fragments thereof, may also be used in gene therapy carried out by homologous recombination or site-directed mutagenesis. See generally Thomas & Capecchi, *Cell* 51, 503–512 (1987); Bertling, *Bioscience Reports* 7, 107–112 (1987); Smithies et al., *Nature* 317, 230–234 (1985).

Oligonucleotides of the present invention are useful as diagnostic tools for probing GalR2 gene expression in tissues. For example, tissues are probed in situ with oligonucleotide probes carrying detectable groups by conventional autoradiographic techniques, as explained in greater detail in the Examples below, to investigate native expression of this receptor or pathological conditions relating thereto. Further, chromosomes can be probed to investigate the presence or absence of the GalR2 gene, and potential pathological conditions related thereto, as also illustrated by the Examples below. Probes according to the invention should generally be at least about 15 nucleotides in length to prevent binding to random sequences, but, under the appropriate circumstances may be smaller.

The invention also provides antibodies that are immunologically reactive to a mammalian GalR2, preferably rat or human GalR2. The antibodies provided by the invention are raised in animals by inoculation with cells that express a mammalian GalR2 or epitopes thereof, using methods well known in the art. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses a mammalian GalR2, or any cell or cell line that expresses a mammalian GalR2 or any epitope thereof as a result of molecular or genetic engineering, or that has been treated to increase the expression of a mammalian GalR2 by physical, biochemical or genetic means. Preferred cells are human cells, most preferably HEK 293 cells that have been transformed with a recombinant expression construct comprising a nucleic acid encoding a mammalian GalR2, preferably a rat or human GalR2, and that express the mammalian GalR2 gene product.

The present invention provides monoclonal antibodies that are immunologically reactive with an epitope of mammalian GalR2 or fragment thereof and that is present on the surface of mammalian cells, preferably human or mouse cells. These antibodies are made using methods and techniques well known to those of skill in the art.

Monoclonal antibodies provided by the present invention are produced by hybridoma cell lines, that are also provided by the invention and that are made by methods well known in the art. Hybridoma cell lines are made by fusing individual cells of a myeloma cell line with spleen cells derived from animals immunized with cells expressing the GalR2 receptor, preferably rat or human cells, as described above. The myeloma cell lines used in the invention include lines derived from myelomas of mice, rats, hamsters, primates and humans. Preferred myeloma cell lines are from mouse. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of a mammalian GalR2.

The present invention encompasses fragments of the antibody that are immunologically reactive with an epitope of a mammalian GalR2. Such fragments are produced by any number of methods, including but not limited to proteolytic cleavage, chemical synthesis or preparation of such fragments by means of genetic engineering technology. The present invention also encompasses single-chain antibodies that are immunologically reactive with an epitope of a mammalian GalR2 made by methods known to those of skill in the art.

The present invention also encompasses an epitope of a mammalian GalR2 that is comprised of sequences and/or a conformation of sequences present in the mammalian GalR2 molecule. This epitope may be naturally occurring, or may be the result of proteolytic cleavage of the mammalian GalR2 molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to an epitope that is a mammalian GalR2. The chimeric antibodies embodied in the present invention include those that are derived from naturally occurring antibodies as well as chimeric antibodies made by means of genetic engineering technology well known to those of skill in the art.

Also provided by the present invention are non-human transgenic animals grown from germ cells transformed with the GalR2 nucleic acid sequence according to the invention and that express the GalR2 receptor according to the invention and offspring and descendants thereof. Also provided are transgenic non-human mammals comprising a homologous recombination knockout of the native GalR2 receptor, as well as transgenic non-human mammals grown from germ cells transformed with nucleic acid antisense to the GalR2 nucleic acid of the invention and offspring and descendants thereof. Further included as part of the present invention are transgenic animals which the native GalR2 receptor has been replaced with the human homolog. Of course, offspring and descendants of all of the foregoing transgenic animals are also encompassed by the invention.

Transgenic animals according to the invention can be made using well known techniques with the nucleic acids disclosed herein. E.g., Leder et al., U.S. Pat. Nos. 4,736,866 and 5,175,3 83; Hogan et al., Manipulating the Mouse Embryo, A Laboratory Manual (Cold Spring Harbor Laboratory (1986)); Capecchi, *Science* 244, 1288 (1989); and Zimmer and Gruss, *Nature* 338, 150 (1989). Such transgenic animals are useful for screening for and determining the physiological effects of GalR2 receptor agonists and antagonist Consequently, such transgenic animals are useful for developing drugs to regulate physiological activities in which galanin participates.

The following Examples are provided for illustrative purposes only and are not intended, nor should they be construed, as limiting the invention in any manner.

EXAMPLES

Example 1

Isolation and Sequencing of Rat GalR2 Receptor
Isolation of rat hypothalamus mRNA and
construction of cDNA library An expression cloning strategy was used to clone the novel galanin receptor from a rat hypothalamus cDNA library. RNA was obtained from 9 frozen rat hypothalami weighing a total of 0.87 grams. Poly(A) RNA was isolated directly from the tissue using the Promega PolyATtract System 1000 kit (Promega (Madison, Wis.) Z5420). The hypothalami were homogenized in 4 mL of 4M guanidine thiocyanate-25 mM sodium citrate, pH 7.1-2% β-mercaptoethanol using a Polytron at full-speed for approximately 1 minute. To the homogenized tissue 8 mL of 4M guanidine thiocyanate-25 mM sodium citrate, pH 7.1-1% β-mercaptoethanol which had been preheated to 70° C. was added. After mixing thoroughly, 870 pmol biotinylated oligo(dT) was added; the mixture was incubated at 70° C. for 5 minutes. The homogenate was subjected to centrifugation at 12000×g for 10 minutes at room temperature; the homogenate was transferred to a clean tube and 10.44 mL Streptavidin MAGNESPHERE® Paramagnetic Particles (SA-PMPs) which had been prepared as per the published protocol was added. (Promega Corporation (Madison, Wis.) published protocol TM 228). The homogenate and SA-PMPs were incubated together for 2 minutes at room temperature after which the homogenate was decanted while the SA-PMP-biotinylated oligo(dT)-hypothalamic poly(A) RNA complex was retained in the tube by a magnetic stand. The complex was washed as per the protocol, after which the RNA was precipitated and resuspended in water. 25 micrograms of this poly(A) RNA was used by Invitrogen (Invitrogen Corporation, San Diego, Calif.) to prepare a cDNA expression library. The protocols used by Invitrogen to prepare the cDNA library are essentially based upon the procedures of Okayama and Berg (*Molec. Cell. Biol.* 2, 161 (1982)) and Gubler and Hoffman (*Gene* 25, 263 (1983)) (Invitrogen Corporation (San Diego, Calif.) publications 130813sa and 130928sa). An oligo(dT) anchor primer was used for reverse transcription, and the library was cloned unidirectionally into pcDNA3 vector which contains a CMV (cytomegalovirus) promoter for eukaryotic expression. The cDNA library had $5.3 \times 10^5$ primary recombinants with an average insert size of 2.59 kb.

Isolation of a Novel Galanin Receptor cDNA clone
1. Homology Cloning Strategy

In order to isolate novel receptor(s) for galanin, approximately 2 million phage plaques of a rat small intestine library (Stratagene (La Jolla, Calif.) 936508) were screened with rat GalR1 coding sequence DNA as probe under low stringency conditions (30% formamide, 6×SSC (0.9M NaCl/0.09M NaCitrate), 0.1% N-lauroyl sarcosine, 0.2% SDS, 3% blocking reagent.) The probe was prepared by digesting the parent GalR1 plasmid with SacI and AccI, separating the fragments by agarose gel electrophoresis, and purifying the 1-kb SacI-AccI fragment from the gel. The probe was labeled with digoxigenin dUTP according to the manufacturer's instructions (GENIUS Kit, Boehringer Mannheim, Indianapolis, Ind., PN 1093 657). The filter lifts, denaturation, neutralization, hybridization, and washing were done according to the manufacturer's instructions except that hybridization was done at 30° C. and the washes were performed twice for 40 minutes each: once at room temperature; the second at 37° C.

One plaque containing DNA homologous to the probe was purified and subcloned into pBluescript vector (Stratagene (La Jolla, Calif.) 212206) by standard molecular biological techniques. This clone, designated SI2112, was subjected to sequence analysis and was found to contain a sequence which had characteristics of a novel, but truncated member of the G-protein-coupled 7TMD receptor family. This clone was later used as probe to determine the identity of a novel galanin-binding clone (Y107) found in the expression cloning strategy (see below.)

2. Expression Cloning Strategy

The rat hypothalamus cDNA library was plated on the Luria Broth/Ampicillin (GIBCO) plates in pools of 1,000 independent colonies. The plates were incubated at 37° C. for about 20 hours and the bacteria from each plate were scraped in 4–5 ml LB/Ampicillin media. Two ml of the bacteria samples were used for plasmid preparation and one ml of each pool was stored at −80° C. in 15% glycerol.

COS-7 cells were grown in Dulbecco's Modified Eagle Medium (DMEM, GIBCO (Gaithersburg, Md.) 11965-092), 10% fetal bovine serum (GIBCO (Gaithersburg, Md.) 16000-028), and 1× antibiotic/antimycotic solution (GIBCO (Gaithersburg, Md.) 15240-039). Cells were maintained by trypsinizing and splitting at 50 to 70% confluency.

Twenty-four hours before transfection, cells were plated into flaskette chambers (Nunc, Inc. (Naperville, Ill.) 177453) at $3 \times 10^5$ cells/flaskette (equivalent to $3 \times 10^4$ cells/cm$^2$). Two µg of plasmid DNA from each pool was transfected into the cells using 10 µl of Lipofectamine (GIBCO (Gaithersburg, Md.) 18324-012) according to the manufacturer's protocol.

Forty-eight hours after transfection, the [$^{125}$I]galanin binding assay was performed in the flaskette chamber. The cells were washed once with 25 mM Tris-HCl, 10 mM MgCl$_2$, pH 7.4, and blocked for 15 minutes with 1 ml total binding buffer (25 mM Tris-HCl, 10 mM MgCl$_2$, 1% bovine serum albumin, pH 7.4) at room temperature. After aspirating off the blocking solution, 1 ml of binding buffer containing 100 pM $^{125}$I-hGalanin (NEN DuPont (Boston, Mass.) NEX-333) was added and flasks were incubated at room temperature for 90 minutes. Following the incubation, the labeling buffer was removed and the flaskettes were rinsed (approximately 2 ml, per flaskette) four times with ice-cold binding buffer. After a final rinse with ice-cold phosphate buffered saline (PBS)(GIBCO (Gaithersburg, Md.) 14190-136), the cells were fixed with ice-cold PBS/1% glutaraldehyde (Sigma (St. Louis, Mo.) G5882). The solution was removed and residual glutaraldehyde rinsed away with one wash of ice-cold PBS/0.5 M Tris (pH 7.5) followed by one wash of ice-cold PBS. After separating the slide bases from their tops, the slides were dipped in 0.5% gelatin at 42° C. and dried under vacuum. The dried slides were dipped in photographic emulsion (NTB-2) (Kodak (Rochester, N.Y.) 165 4433) diluted 1:1 in 0.02% Aerosol-OT (Sigma (St. Louis, Mo.) A6627) at 42° C., dried at room temperature for 1 hour, and exposed in the darkbox for four or five days at 4° C. After sufficient exposure time, the darkbox was brought to room temperature for 1 hour after which the slides were developed in D-19 developer (Kodak (Rochester, N.Y.) 146 4593) for three minutes at 15° C., placed in fixer (Kodak (Rochester, N.Y.) 197 1746) for three minutes at 15° C., washed in water, and air dried. Cells were stained with Diff-Quik stain set (Baxter (McGaw Park, Ill.) B4132-1) and air dried. Slides were dipped into xylenes and mounted with DPX mountant (Electron Microscopy Sciences (Fort Washington, PA) 13510). Positive cells were identified using dark field microscopy.

Two positive pools were identified. Since the hypothalamus could express different subtypes of galanin receptor, we analyzed the positive pools for GalR1 receptors by PCR and homology. Of the 2 positive pools tested as described above, 1 contained GalR1 as determined by PCR and homology analyses. However, the other pool (Y107) was negative for GalR1 by PCR, but homologous to SI2112 probe (see Homology strategy, above). Because: 1) SI2112 sequence indicated it was likely a novel, albeit truncated and unexpressible, G-protein-coupled receptor; 2) pool Y107 DNA showed homology to the SI2112 probe; and, 3) DNA from pool Y107, when used to transiently transfect COS-7 cells, conferred the ability upon the cells to bind galanin, it was deduced that the clone within pool Y107, which conferred galanin-binding ability when expressed, was likely to be an expressible version of the SI2112 clone. Therefore, clones from pool Y107 were probed with radiolabeled DNA prepared from SI2112, and a single clone hybridizing to the SI2112 probe was purified from non-homologous clones. This clone was called Y107.

Sequence analysis of clone Y107 (SEQ ID NO: 3) revealed the presence of one intron of 489-bp length, beginning after nucleotide 384 (the second nucleotide of the codon for amino acid 133, an arginine residue). Using Y107 DNA as probe, an intronless version of the Y107 cDNA was obtained from a PC12 cell cDNA library by homology cloning. The first intronless version of the Y107 was in the pSV-SPORT vector (GIBCO (Gaithersburg, Md.) 15386-014); the complete cDNA insert of this clone was subcloned into the pcDNA3 vector (Invitrogen (San Diego, Calif.) V790-20) in order to maintain, for subsequent pharamacological analyses, common vector and promoter (CMV) backgrounds amongst our clones. The intronless clone in pSV-SPORT was designated BMB77. sv40; the intronless clone contained within pcDNA3 is named BMB77. Clones BMB77 and Y107 differ by one amino acid in sequence. Pharmacological analyses have been performed with both the Y107 (SEQ ID NO: 3 and 4) and BMB77 (SEQ ID NO: 1 and 2) clones.

DNA and Peptide Sequences Analysis

Plasmid DNA was sequenced by Lark Technologies Inc. (Houston, Tex.) and Biotechnology Resource Laboratory of Yale University (New Haven, Conn.) using Sequenase Kit (US Biochemical (Cleveland, Ohio) 70770) or Applied Biosystems' automatic sequencer system (Model 373A). The peptide sequence was deduced from the long open-reading-frame of the nucleotide sequence. DNA and peptide sequences were analyzed using the GCG program (Genetics Computer Group, Madison, Wis.). The results are embodied in SEQ ID NO: 1 (the nucleic acid sequence of clone BMB77), SEQ ID NO: 2 (the amino acid sequence of clone BMB77), SEQ ID NO: 3 (the nucleic acid sequence of clone Y107), and SEQ ID NO: 4 (the amino acid sequence, omitting the putative intronic region, of clone Y107).

Example 2

Pharmacological Characterization of the Novel Rat Galanin Receptor

Transient Transfection

Monkey kidney cells (COS-7) were maintained in T-175 cm$^2$ flasks (Nunc, Inc. (Naperville, Ill.) 171226) at 37° C. with 5% $CO_2$ in a humidified atmosphere. Cells were grown in Dulbecco's Modified Eagle Medium (DMEM) (GIBCO (Gaithersburg, Md.) 11965-092) supplemented with 2 mM glutamine, 10% fetal bovine serum, 1 mM sodium pyruvate and a antibiotic/antimycotic comprised of pennicillin/streptomycin/amphotericinB (GIBCO, Gaithersburg, Md., PN 15240-013). Cells at 70% confluency were transfected with rat GalR2 DNA using the Lipofectamine reagent (GIBCO (Gaithersburg, Md.) 18324-012). 15 µg of DNA and 90 µl of lipofectamine were added to each flask. Media was replaced 24 hours post transfection, and membranes were harvested 24 hours later.

Membrane Preparation

The media was removed from each flask of transfected cells, and the cells were washed twice with 20 ml ice-cold phosphate buffered saline. The cells were scraped from the flask in 5 ml of Tris buffer (20 mM Tris-HCl, 5 mM EDTA, pH 7.7), and then transferred to a centrifuge tube. Each flask was rinsed with an additional 5 ml of Tris buffer, and combined in the centrifuge tube. The cells were homogenized in a Polytron PT-3000 (Brinkman Instruments, Mill Valley, N.Y.) for 2×10 seconds (12 mM probe, 7000–8000 rpm) and centrifuged at 20,000×g for 30 minutes at 4° C. The pellet was resuspended in fresh Tris buffer, and centrifuged again at 20,000×g for 30 minutes at 4° C. Protein concentration was measured using the Bio-Rad kit according to the standard manufacturer's protocol (Bio-Rad Laboratories (Hercules, Calif.) 500-0001) using bovine IgG as the standard.

[$^{125}$I]Galanin Binding Assay for rat GalR1 and rat GalR2 Clones

The binding assays were performed on 96-well plates (GF/C Millipore Corp., Bedford, MA PN MAFC NOB 50) pretreated with 0.3% polyethylenimine (PEI) for at least 3 hours prior to use. The PEI was aspirated from the plates on a vacuum manifold, and the wells were rinsed with 200 µl of ice-cold binding buffer (25 mM Tris, 10 mM $MgCl_2$, 0.1% BSA, pH 7.4) immediately before samples were added to the wells. For competition assays, increasing concentrations of peptide were incubated with [$^{125}$I]hGalanin (NEN DuPont (Boston, Mass.) NEX333) and membrane. In a final volume of 200 µl, samples consisted of ~2.5 µg of protein, 50 pM [$^{125}$I]hGalanin, and peptide dilution or binding buffer. Nonspecific binding was defined by 100 nM rat galanin. Samples were incubated for 90 minutes at room temperature with constant shaking. To terminate the reaction, samples were aspirated on a vacuum manifold and rinsed with 3×200 µl ice-cold buffer. Samples were then counted on a gamma counter to quantitate the amount of radioactivity. Rat galanin, fragment peptides (1 -15)galanin, (1-12)galanin, (1-10)galanin, chimeric peptide M40, (2-29) rat galanin, (3-29)rat galanin, (5-29)rat galanin, (9-29)rat galanin, (10-29)rat galanin, (2-30)human galanin, and (3-30) human galanin were synthesized at Bayer Corp. (West Haven, Conn.). All other peptides were purchased from either Peninsula (Belmont, Calif.) or Bachem (Torrance, Calif.).

In Vitro Pharmacology

Table 1 presents the $IC_{50}$ values (50% inhibition of specific binding, as determined using nonlinear regression analysis) of various peptides, fragments and chimeras for [$^{125}$I]hGalanin binding to membranes of clone Y107, clone BMB77 and rat GalR1 transiently expressed in COS-7 cells. The preliminary pharmacological binding profile for rat GalR2 differs from rat GalR1, such that galanin itself has about 10-fold lower affinity for GalR2, as do the chimera C7 and rat(1-16)galanin. Rat clone BMB77 has a binding profile very similar to the intron-containing, putative allelic variant, rat clone Y107, with the exception of (1-12)galanin.

TABLE 1

| PEPTIDE | Rat GalR2 [clone Y107] $IC_{50}$ value (nM) | Rat GalR2 [clone BMB77] $IC_{50}$ value (nM) | Rat GalR1 [cloned] $IC_{50}$ value (nM) |
|---|---|---|---|
| r(1-29)galanin | 0.46 (0.32,0.60) | 0.59 (0.56,0.61) | 0.061 ± 0.007 |
| h(1-30)galanin | 0.29 | ND | 0.037 (0.040,0.033) |
| r(2-29)galanin | 0.41 | ND | 1.6 ± 0.42 |
| M35 | 0.72 | 0.68 | ND |
| M40 | 0.78 (0.75,0.81) | 0.71 | 0.32 ± 0.10 |
| r(1-16)galanin | 0.86 (0.97,0.75) | 1.6 | 0.18 ± 0.02 |
| h(2-30)galanin | 0.94 | ND | 1.9 ± 0.26 |
| (1-15)galanin | 1.0 (1.1,0.99) | 1.2 | 1.1 ± 0.27 |
| (1-12)galanin | 1.6 (1.8,1.4) | 16 | 24 (22,25) |
| C7 | 2.6 | 3.0 | 0.26 ± 0.02 |
| M15 | 7.0 | ND | 2.0 (1.5,2.4) |
| (1-10)galanin | 240 (284,195) | 403 | ND |
| r(3-29)galanin | >1000 | ND | >1000 |
| h(3-30)galanin | >1000 | ND | >1000 |
| r(5-29)galanin | >1000 | ND | >1000 |
| r(9-29)galanin | >1000 | ND | >1000 |
| r(10-29)galanin | >1000 | ND | >1000 |

Table 1 shows that $IC_{50}$ values for the various peptides for [$^{125}$I]hGalanin binding to rat GalR1 and GalR2 clones transiently expressed in COS-7 cells. The averages±standard error of the mean (SEM) represent values from at least three independent experiments. Two independent experiments are represented by the average, followed by the individual values in parentheses. Remaining values without SEM are from a single experiment. Peptide species are indicated with the following prefixes: r=rat, h=human. ND=not determined Abbreviations of Chimers:

M15=(1-13)Galanin+(5-11)Substance P=Galantide (see Bartfai, Tips 13, 312–317 (1992)

M35=(1-13)Galanin+(2-9)Bradykinin (Bartfai, infra)

M40=(1-13)Galanin+ProPro(AlaLeu)$_2$Ala amide (Bartfai, infra)

C7=(1-13)Galanin+santide (see Crawley,*Brain Research* 600, 268–272 (1993)

Having now fully described this invention, it will be appreciated by those skilled in the art that the same can be performed with any wide range of equivalent parameters of composition, conditions, and methods of preparing such recombinant molecules, vectors, transformed hosts and proteins without departing from the spirit or scope of the invention or any embodiment thereof

We claim:

1. A purified and isolated galanin receptor 2 (GalR2) protein comprising SEQ ID NO:2.

2. A purified and isolated GalR2 protein comprising SEQ ID NO:4.

* * * * *